United States Patent [19]

Kampf

[11] 4,434,310
[45] Feb. 28, 1984

[54] PROCESS FOR THE ISOMERIZATION OF ISOLATED DOUBLE BONDS TO CONJUGATED DOUBLE BONDS IN OPTIONALLY SUBSTITUTED CYCLOOCTADIENES

[75] Inventor: Wolfgang Kampf, Haltern, Fed. Rep. of Germany

[73] Assignee: Chemische Werke Huels Aktiengesellschaft, Marl, Fed. Rep. of Germany

[21] Appl. No.: 457,550

[22] Filed: Jan. 13, 1983

[30] Foreign Application Priority Data

Jan. 13, 1982 [DE] Fed. Rep. of Germany ....... 3200783

[51] Int. Cl.$^3$ .............................................. C07C 5/30
[52] U.S. Cl. .................................. 585/377; 585/601; 585/664; 585/665
[58] Field of Search ............... 585/377, 601, 664, 665, 585/666, 667, 668, 669, 670, 671

[56] References Cited

U.S. PATENT DOCUMENTS

| 3,080,432 | 3/1963 | Voltz et al. ......................... 585/377 |
| 3,124,621 | 3/1964 | Crain et al. ......................... 585/377 |
| 3,309,410 | 3/1967 | Schriesheim et al. ............... 585/377 |
| 3,441,629 | 4/1969 | Zuech ................................. 585/665 |
| 3,507,928 | 4/1970 | Rinehart ............................. 585/377 |
| 3,767,716 | 9/1971 | Tsuneyuki ........................... 585/377 |
| 3,856,877 | 12/1974 | Otsuki et al. ........................ 585/601 |
| 3,872,178 | 3/1975 | Tabler ................................. 585/601 |

FOREIGN PATENT DOCUMENTS

| 697527 | 11/1964 | Canada .............................. 585/377 |
| 1337889 | 8/1962 | France ................................ 585/377 |
| 973850 | 10/1964 | United Kingdom ................ 585/377 |
| 1033760 | 6/1966 | United Kingdom ................ 585/377 |
| 577199 | 10/1977 | U.S.S.R. ............................. 585/664 |

Primary Examiner—Delbert E. Gantz
Assistant Examiner—A. Pal
Attorney, Agent, or Firm—Millen & White

[57] ABSTRACT

A process for the isomerization of isolated double bonds to conjugated double bonds in optionally substituted cyclooctadienes using alkali metal or alkaline earth metal amides, if desired in the presence of a solvent, requires that the alkali metal or alkaline earth metal amide be produced with exclusion of moisture and under a protective gas atmosphere in the presence of the cyclooctadiene to be isomerized; and that the isomerization be conducted at temperatures of 70°–200° C.

18 Claims, No Drawings

PROCESS FOR THE ISOMERIZATION OF ISOLATED DOUBLE BONDS TO CONJUGATED DOUBLE BONDS IN OPTIONALLY SUBSTITUTED CYCLOOCTADIENES

BACKGROUND OF THE INVENTION

The individual isomeric forms of unconjugated cyclooctadienes, such as, for example, cis,cis-1,4-and cis,-cis-1,5-cyclooctadiene, are valuable starting materials for various syntheses. In some cases, for example for polymerizations or epoxidations, it is, however, desirable to have the double bonds present in conjugation.

All methods heretofore known for the isomerization of isolated to conjugated double bonds in optionally substituted cyclooctadienes, however, are more or less hampered by deficiencies. Thus, in the process according to U.S. Pat. No. 3,398,205 wherein iron pentacarbonyl is primarily used as the catalyst, problems are encountered in the clean separation of the isomerized product on account of the volatility of the catalyst. In the method disclosed in U.S. Pat. No. 3,767,716, wherein the catalyst is alkali metal hydroxide applied together with an alkali metal or aluminum oxide, there is a different drawback. Here, the catalysts are difficult to handle technically since they are very sensitive to air and entail a certain risk. Finally, in the process of U.S. Pat. No. 3,124,621 wherein isomerization is conducted using alkali or alkaline earth metal amides in the presence of ammonia or amines as the solvent, relatively high catalyst concentrations must be employed to attain an industrially interesting degree of isomerization. An additional disadvantage in this process is the necessity of using relatively large quantities of a solvent.

SUMMARY OF THE INVENTION

It is therfore an object of this invention to provide a process for the isomerization of isolated double bonds to conjugated double bonds in optionally substituted cyclooctadienes which overcomes or ameliorates the foregoing disadvantages, e.g., wherein the amount of readily accessible catalysts is reduced without prolonging the reaction period, and wherein the use of a solvent, required in the process of the relevant state of the art, can be omitted.

Upon further study of the specification and appended claims, further objects and advantages of this invention will become apparent to those skilled in the art.

These objects have been attained by providing a process for the isomerization of isolated double bonds to conjugated double bonds in optionally substituted cyclooctadienes using an alkali metal or alkaline earth metal amide, optionally in the presence of a solvent, comprising producing the alkali metal or alkaline earth metal amide under conditions of exclusion of moisture and under a protective gas atmosphere in the presence of the cyclooctadiene to be isomerized; and conducting the isomerization at temperatures of 70°–200° C.

DETAILED DISCUSSION

A surprising aspect of this process is that, in general, a preformed catalyst displays a higher activity than a catalyst produced in situ. The opposite effect is observed here.

Cyclooctadienes suitable for use in this invention include not only all the possible unsubstituted isomers, but also the counterparts which carry alkyl group substituents, preferably of up to 5 carbon atoms each. Cyclooctadienes with isolated double bonds include, for example, cis,cis-1,5-cyclooctadiene (COD-1,5), cis,-cis-3-methyl-1,5-cyclooctadiene, cis,cis-3,7-diethyl-1,5-cyclooctadiene, cis,cis-3,4,8-tri-n-propyl-1,5-cyclooctadiene, cis,cis-3,4,7,8-tetra-n-pentyl-1,5-cyclooctadiene, cis,cis-1,2,3,4,5,6,7,8-octamethyl-1,5-cyclooctadiene, cis,trans-1,5-cyclooctadiene, cis,trans-3-n-butyl-1,5-cyclooctadiene, cis,trans-4,8-di-n-pentyl-1,5-cyclooctadiene, cis,trans-3,4-dimethyl-1,5-cyclooctadiene, cis,trans-1,2,5,6-tetraisopropyl-1,5-cyclooctadiene, cis,trans-8-tert-butyl-1,5-cyclooctadiene, cis,trans-1,2,3,4,5,6,7,7,8,8-deca-n-pentyl-1,5-cyclooctadiene, cis,trans-1,2-diethyl-1,5-cyclooctadiene, cis,cis-1,2-dimethyl-1,4-cyclooctadiene, cis,cis-3-ethyl-1,4-cyclooctadiene, cis,cis-3,8,8-tri-n-propyl-1,4-cyclooctadiene, cis,cis-1,2,4,5,6,6,7,7,8,8,-decamethyl-1,4-cyclooctadiene, cis,cis-1,4-cyclooctadiene, cis,-cis-1,2,3,3,-tetra-n-butyl-1,4-cyclooctadiene, cis,cis-1,2,4,5-tetra-n-pentyl-1,4-cyclooctadiene, cis,cis-1,2,3,3,4,5,6,7,8-nona-n-propyl-1,4-cyclooctadiene, cis,-trans-1,2,7,7-tetramethyl-1,4-cyclooctadiene, cis,trans-6,6,7,7,8,8-hexa-n-butyl1,4-cyclooctadiene, cis,trans-1,2,3,4-tetra-n-pentyl-1,4-cyclooctadiene, cis,trans-1,2,4,5,6,6,8-heptaethyl-1,4-cyclooctadiene, cis, trans-8-tert-butyl-1,4-cyclooctadiene, cis,trans-3,3-di-secpentyl-1,4-cyclooctadiene, cis,trans-3,3,7,8-tetraethyl-1,4-cyclooctadiene, cis,trans-1,2,3,3,4,5,6,7,7-nona-n-propyl-1,4-cyclooctadiene, or cis,trans-1,4-cyclooctadiene.

Starting materials for the formation of the amide acting as the isomerization catalyst include, on the one hand, the corresponding suitable amine and, on the other hand, alkali and alkaline earth metals and/or the hydrides and organometallic compounds thereof.

In principle, all mono- or polyfunctional amines carrying at least one primary or secondary amino group are suitable. However, for reasons of process technology, amines are preferred which have a boiling point which is higher than that of the cyclooctadiene to be isomerized. Typical amines include: ethylenediamine, dipropylenetriamine, cyclohexylamine, n-butylamine, 3-aminopyridine, di-n-butylamine, 1,3- and 1,2-propylenediamine, 1,2-diaminocyclohexane, 1,4-diaminocyclohexane, triethylenetetramine, n-propylamine, di-n-hexylamine, or sec-octylamine, etc. Among these amines, cited merely as examples, dipropylenetriamine is especially preferred. As can be seen a very diverse spectrum of amine structures are suitable including aromatic, aliphatic, acyclic, cyclic, heterocyclic, mono-, poly-, primary,secondary, etc., amines all of which must also be reaction compatible, of course. A further listing of suitable amines can be ascertained by reference to U.S. Pat. No. 3,124,621 whose disclosure is entirely incorporated by reference herein.

Suitable alkali metals are lithium, sodium, potassium, rubidium, and cesium; suitable alkaline earth metals are magnesium, calcium, strontium, and barium. They are generally used in powder form with an average particle diameter of $<100$ $\mu$m, preferably 5–50 $\mu$m. The hydrides derived from these metals, which can also be used, correspond, as is known, in case of the alkali metal hydrides to the general formula MeH and in case of the alkaline earth metal hydrides to the general formula MeH$_2$ (for more details see "Ullmanns Encyklopadie der technischen Chemie" [Ullman's Encyclopedia of Technical Chemistry] [1957] Vol. 8, pp. 722–728). Suitable organometallic compounds usable in the process of this invention include, on the one hand, the alkali metal alkyls of up to 8 carbon atoms in the alkyl group, e.g. butyllithium, amyllithium, and amylsodium, and on the other hand the organometallic alkaline earth metal compounds of the general formulae $MeR_2^1$ and $MeR^2X$, wherein $R^1$ is $C_1$- to $C_8$- alkyl, $R^2$ is $C_1$- to $C_8$-alkyl or an aromatic residue of up to 10 carbon atoms (e.g., phenyl or naphthyl), and X is chlorine or bromine. A preferred representative of the compounds of the formula $MeR^2X$ is ethylmagnesium bromide. Sodium or potassium powder and sodium hydride are preferably employed.

In general, the procedure of the process of this invention is to provide in a reaction chamber, for example, at room temperature, the dry ($H_2O$ content <10 ppm) cyclooctadiene with isolated double bonds under conditions of exclusion of moisture and under an inert gas atmosphere, e.g. under nitrogen or argon, and then to add the two compounds, which will form the amide, in any desired sequence.

The alkali or alkaline earth metal and/or its aforementioned compounds are added in such a quantity that the molar ratio thereof to cyclooctadiene ranges from 0.005:1 to 0.1:1, preferably from 0.01:1 to 0.05:1. The molar ratio of alkali or alkaline earth metal per se or compound to the amine is to be in the range from 1:0.5 to 1:10, preferably from 1:1 to 1:5.

If the metal or the metallic compound and the amine are added to the cyclooctadiene at a temperature lying below the temperature interval within which isomerization takes place at adequate speed, the mixture is subsequently heated to the optimum isomerizing temperature and/or to the temperature most favorable for the course of the reaction. It is maintained at such temperature until the desired or attainable degree of isomerization has been achieved.

The isomerization is generally carried out in a temperature range from 70° to 200° C, preferably in a range from 80° to 160° C. The reaction times are generally 5 minutes to 24 hours in dependence on the selected process conditions (location and concentration of catalyst, temperature, etc.).

Although the addition of a solvent is not required in the process of this invention, it is fundamentally possible to do so. Suitable solvents which, of course, must be extensively free of water just as the cyclooctadiene utilized (e.g., <10 ppm $H_2O$) include, for example, aliphatic and aromatic hydrocarbons, such as, for example, cyclohexane and toluene.

In general, the process of this invention is operated without the use of excess pressure. However, if the isomerization temperature is above the boiling temperature of the amine used in excess to the metal and/or the metallic compound and/or above the mixed boiling point resulting from cyclooctadiene with isolated double bonds and cyclooctadiene with conjugated double bonds and/or above that of the optionally used solvent, then an autoclave is necessary.

A reacted batch is generally worked up by distillation. In an optional version of the process of this invention, the isomerized product (e.g., COD-1,3) resulting, for example, when using cis,cis-1,5-cyclooctadiene, is continuously removed by distillation up to a certain point of catalyst exhaustion. Fresh cis,cis-1,5-cyclooctadiene is used to replace the reacted starting material.

Since the cis,cis-form represents the most stable form of cyclooctadienes with conjugated double bonds, the resultant conjugated diene is a cis,cis-1,3-cyclooctadiene. The basic skeleton thus has the following formula:

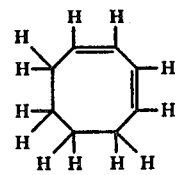

Cyclooctadienes with conjugated double bonds, preferably cis,cis-1,3-cyclooctadiene, can be utilized, inter alia, for the stabilization of copolymers of unsaturated nitriles and monovinylidene aromatics against discoloring due to heat and/or aging as described in U.S. Pat. No. 3,444,126 whose disclosure is incorporated by reference herein.

Without further elaboration, it is believed that one skilled in the art can, using the preceding description, utilizxe the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicatd, all parts and percentages are by weight. Room temperature is 20° C.

EXAMPLE 1

A flask equipped with thermometer, agitator, and reflux condenser is charged at room temperature under exclusion of moisture and under a nitrogen atmosphere ($N_2$ atmosphere) with 1,852 millimoles of dry ($H_2O$ content <10 ppm) cis,cis-1,5-cyclooctadiene (COD-1,5) 200 g, 40 millimoles of sodium hydride (NaH) 0.96 g, and 102 millimoles of dipropylenetriamine (DPTA) 13.37 g.

Under agitation, the mixture is heated to 100° C. and maintained at this temperature for 5 hours. The color hue of the content of the flask changes after about 1 hour from light-brown to dark-brown. After various time periods from the time when the temperature reaches 100° C., samples are withdrawn and analyzed by gas chromatography. Table 1 contains the thus-determined data.

TABLE 1

| Time (min) | COD-1,3 (% by Weight) | COD-1,5 (% by Weight) |
|---|---|---|
| 15 | 15.6 | 77.8 |
| 30 | 32.6 | 60.7 |
| 60 | 72.4 | 21.6 |
| 120 | 90.8 | 4.0 |
| 180 | 93.1 | 1.9 |
| 240 | 93.8 | 1.2 |
| 300 | 94.1 | 1.0 |

The residual proportions are essentially high-boiling compounds.

COMPARATIVE EXAMPLE A

In the apparatus described in Example 1, 40 mmol of NaH and 102 mmol of DPTA are first of all allowed to react for 30 minutes at 100° C. in accordance with the mode of operation described in U.S. Pat. No. 3,124,621. Then, at the 100° C. temperature and under an $N_2$ atmosphere, 1,852 mmol of COD-1,5 is added thereto. During the testing period at 100 C., again being 5 hours, the COD-1,5 content, at 93.5% by weight and the COD-1,3 content, at 0.03% by weight, remained parctically constant.

EXAMPLE 2-5

Example 1 is repeated, respectively at a temperature different from 100° C. Table 2 indicates the weight percentages of COD-1,5 and COD-1,3 obtained after an operating period of 5 hours.

TABLE 2

| Example No. | T (°C.) | COD-1,3 (% by Weight) | COD-1,5 (% by Weight) |
|---|---|---|---|
| 2 | 70 | 0.1 | 94.4 |
| 3 | 80 | 64.5 | 29.8 |
| 4 | 90 | 92.1 | 2.5 |
| 5 | 144 | 87.9 | 8.7 |

If the isomerization is conducted under reflux temperture, the increasing isomerization can be recognized from the dropping boiling temperature, since COD-1,3 boils 7° C. lower than COD-1,5.

COMPARATIVE EXAMPLE B

Comparative Example A is repeated, except that the mixture is maintained at the boiling temperature of COD-1,5 (151° C.) during the 5-hour testing period. Again, no appreciable isomerization occurs. The COD-1,3 contents of all samples drawn at the points in time indicated in Example 1 range below 0.5% by weight.

EXAMPLES 6-10

Using the same apparatus and the same mode of operation as described in Example 1, the molar amounts of NaH and DPTA and optionally the experimental temperature are varied, with the quantity of COD-1,5 (1,852 mmol) remaining the same. Table 3 shows the results.

TABLE 3

| Example No. | NaH mmol | DPTA mmol | T °C. | COD-1,3 % by Wt. | COD-1,5 % by Wt. |
|---|---|---|---|---|---|
| 6 | 23 | 102 | 146 | 19.4 | 75.5 |
| 7 | 115 | 102 | 144 | 97.6 | 1.2 |
| 8 | 40 | 204 | 145 | 64.3 | 25.5 |
| 9 | 40 | 58 | 145 | 81.9 | 17.7 |
| 10 | 40 | 58 | 100 | 14.8 | 81.5 |

Although the indicated percentages of COD-1,3 and COD-1,5 are the results measured after 5-hour testing period, these values are reached in most cases as early as after 15 minutes.

COMPARATIVE EXAMPLE C

Comparative Example A is repeated, except that 115 mmol of NaH is used instead of 40 mmol of NaH. After a testing period of 15 minutes, a COD-1,3 proportion is measured of 2.0% by weight; after a 5-hour testing period, the measured proportion is 2.5% by weight.

EXAMPLES 11-14

Example 1 is repeated, except using, instead of DPTA, 102 mmol of another amine and making the testing temperature in Examples 12-14 the boiling temperature of the COD mixture rather than 100° C. Table 4 indicates the percentages of COD-1,3 and COD-1,5 after various testing periods.

TABLE 4

| Example No. | Amine | Time min | COD-1,3 % by Wt. | COD-1,5 % by Wt. |
|---|---|---|---|---|
| 11 | Ethylenediamine | 30 | 96.6 | 2.5 |
|  | Ethylenediamine | 300 | 97.7 | 1.0 |
| 12 | n-Butylamine | 300 | 69.7 | 27.5 |
| 13 | Cyclohexylamine | 300 | 94.3 | 0.3 |
| 14 | 2-Aminopyridine | 15 | 66.2 | 31.9 |

EXAMPLES 15-18

Instead of using sodium hydride according to Example 1, different metallic compounds and/or metallic sodium dust are utilized in varying amounts (Table 5, column 3). The apparatus, the conductance of the test, and the amounts of COD-1,5 and DPTA utilized are as described in Example 1. The COD-1,3 and COD-1,5 contents in Table 5 were meausured respectively after 5 hours.

TABLE 5

| Example No. | Type and Amount (mmol) of Metal or Metallic Compound | | COD-1,3 % by Wt. | COD-1,5 % by Wt. |
|---|---|---|---|---|
| 15 | Butyllithium | 80 | 21.3 | 76.6 |
| 16 | Sodium Dust | 80 | 96.2 | 1.4 |
| 17 | Potassium Dust | 120 | 96.3 | 1.3 |
| 18 | Ethylmagnesium Bromide | 120 | 10.5 | 87.2 |

The preceding examples can be repeated with similar success by substituting the generically or specifically discribed reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the isomerization of isolated double bonds to conjugated double bonds in optionally substituted cyclooctadienes using as a catalyst an alkali metal or alkaline earth metal amide, optionally in the presence of a solvent, the improvement wherein the alkali metal or alkaline earth metal amide is prepared in situ with the substantial exclusion of moisture, under a protective gas atmosphere and in the presence of the cyclooctadiene to be isomerized; and wherein the isomerization is conducted at a temperature of 70°-200° C.

2. A process of claim 1, wherein in the in situ production of the alkali or alkaline earth metal amide, the corresponding primary or secondary amine is reacted with an alkali or alkaline earth metal powder, metal hydride, or organometallic compound.

3. A process of claim 2, wherein the primary or secondary amine has a boiling point which is higher than that of the cyclooctadiene to be isomerized.

4. A process of claim 2 wherein the molar ratio of the alkali metal or alkaline earth metal or of the alkali metal or alkaline earth metal compound to the amine is from 1 : 0.5 to 1 : 10.

5. A process of claim 2, wherein the molar ratio of the alkali metal or alkaline earth metal or of the alkali metal or alkaline earth metal compound to the cyclooctadiene to be isomerized is 0.005 : 1 to 0.1 : 1.

6. A process of claim 1, wherein the conjugated cyclooctadiene is a cis,cis-1,3-cyclooctadiene.

7. A process of claim 1, wherein the starting cyclooctadiene containing isolated bonds is cis,cis-1,5-cyclooctadiene, cis, cis-3-methyl-1,5-cyclooctadiene, cis,cis-3,7-diethyl-1,5-cyclooctadiene, cis,cis-3,4,8-tri-n-propyl-1,5-cyclooctadiene, cis,cis-3,4,7,8-tetra-n-pentyl-1,5-cyclooctadiene, cis,cis-1,2,3,4,5,6,7,8-octamethyl-1,5-cyclooctadiene, cis,trans-1,5-cyclooctadiene, cis,trans-3-n-butyl-1,5-cyclooctadiene, cis,trans-4,8-di-n-pentyl-1,5-cyclooctadiene, cis,trans-3,4-dimethyl-1,5-cyclooctadiene, cis,trans-1,2,5,6-tetraisopropyl-1,5-cyclooctadiene, cis,trans-8-tert-butyl-1,5-cyclooctadiene, cis,trans-1,2,3,4,5,6,7,7,8,8-deca-n-pentyl-1,5-cyclooctadiene, cis,trans-1,2-diethyl-1,5-cyclooctadiene, cis,cis-1,2-dimethyl-1,4-cyclooctadiene, cis,cis-3-ethyl-1,4-cyclooctadiene, cis,cis-3,8,8-tri-n-propyl-1,4-cyclooctadiene, cis,cis-1,2,4,5,6,6,7,7,8,8-decamethyl-1,4-cyclooctadiene, cis,cis-1,4-cyclooctadiene, cis,cis-1,2,3,3-tetra-n-butly-1,4-cyclooctadiene, cis,cis-1,2,4,5-tetra-n-pentyl-1,4-cyclooctadiene, cis,cis-1,2,3,3,4,5,6,7,8-nona-n-propyl-1,4-cyclooctadiene, cis,trans-1,2,7,7-tetramethyl-1,4-cyclooctadiene, cis,trans-6,6,7,7,8,8-hexa-n-butyl-1,4-cyclooctadiene, cis,trans-1,2,3,4-tetra-n-pentyl-1,4cyclooctadiene, cis,trans-1,2,4,5,6,6,8-heptaethyl-1,4-cyclooctadiene, cis,trans-8-tert-butyl-1,4-cyclooctadiene, cis,trans-3,3-di-sec-pentyl-1,4-cyclooctadiene, cis,trans-3,3,7,8-tetraethyl-1,4-cyclooctadiene, cis,trans-1,2,3,3,4,5,6,7,7-nona-n-propyl-1,4-cyclooctadiene, or cis,trans-1,4-cyclooctadiene.

8. A process of claim 6, wherein the starting cyclooctadiene containing isloated bonds is cis,cis-1,5-cyclooctadiene.

9. A process of claim 2, wherein the amine is ethylenediamine, dipropylenetriamine, cyclohexylamine, n-butylamine, 3-aminopyridine, di-n-butyl-amine, 1,3-or 1,2-propylenediamine, 1,2-diaminocyclohexane, 1,4-diaminocyclohexane, triethylenetetramine, n-propylamine, di-n-hexylamine, or sec-octylamine.

10. A process of claim 2, wherein the metal-containing reagent is sodium or potassium powder or sodium hydride.

11. A process of claim 2, wherein the organometallic compound is a $C_{1-8}$-alkyl alkali metal or is of the formula $MeR_2^1$ or $MeR^2X$ wherein Me is an alkaline earth metal, $R^1$ is $C_{1-8}$ alkyl, $R^2$ is $C_{1-8}$-alkyl, phenyl or naphthyl and X is Cl or Br.

12. A process of claim 1, wherein the isomerization temperature is 80°–160° C.

13. A process of claim 4, wherein the molar ratio of the alkali metal or alkaline earth metal or of the alkali metal or alkaline earth metal compound to the cyclooctadiene to be isomerized is 0.005 : 1 to 0.1 : 1.

14. A process of claim 13, wherein the molar ratio of the alkali metal or alkaline earth metal or of the alkali metal or alkaline earth metal compound to the amine is from 1 : 1 to 1 : 5 and the molar ratio of the alkali metal or alkaline earth metal or of the alkali metal or alkaline earth metal compound to cyclooctadiene to the isomerized is 0.01 : 1 to 0.05 : 1.

15. A process of claim 1 carried out in a reaction compatible solvent.

16. A process of claim 2 carried out in an autoclave.

17. A process of claim 14, wherein the isomerization temperature is 80°–160° C.

18. A process of claim 1 carried out in the absence of a solvent.

* * * * *